| United States Patent [19] | [11] | 4,232,180 |
|---|---|---|
| Kelly | [45] | Nov. 4, 1980 |

[54] PREPARATION OF UNSYMMETRICAL POLYENES

[75] Inventor: Walter J. Kelly, Stow, Ohio

[73] Assignee: The Goodyear Tire & Rubber Company, Akron, Ohio

[21] Appl. No.: 740,649

[22] Filed: Nov. 10, 1976

Related U.S. Application Data

[63] Continuation of Ser. No. 564,003, Mar. 31, 1975, abandoned.

[51] Int. Cl.$^3$ .............................................. C07C 6/06
[52] U.S. Cl. ................................................... 585/645
[58] Field of Search ...................... 260/683 D, 677 R; 585/645

[56] References Cited

U.S. PATENT DOCUMENTS

| 3,754,046 | 8/1973 | Calderon et al. | 260/677 R |
|---|---|---|---|
| 3,859,263 | 1/1975 | O'Connor et al. | 260/683 D |
| 3,935,179 | 1/1976 | Ofstead | 585/645 X |
| 3,945,986 | 3/1976 | Ofstead | 585/645 X |
| 3,966,637 | 6/1976 | Witte et al. | 260/683 D |

*Primary Examiner*—Delbert E. Gantz
*Attorney, Agent, or Firm*—H. C. Young, Jr.

[57] ABSTRACT

A method directed to the preparation of acyclic polyenes by the reaction of 1-pentene with cyclopentene to form a predominance of unsymmetrical acyclic polyenes.

2 Claims, No Drawings

PREPARATION OF UNSYMMETRICAL POLYENES

This is a continuation, of application Ser. No. 564,003 filed Mar. 31, 1975, now abandoned.

This invention is directed to the preparation of acyclic polyenes by the reaction of acyclic α-olefins with monocycloolefins. More specifically this invention is directed to the preparation of unsymmetrical acyclic polyenes prepared by the reaction of 1-pentene with cyclopentene.

The reaction of 1-pentene with cyclopentene in the presence of cross metathesis catalysts give a product which is a mixture of polyenes which are predominately unsymmetrical. The prior art heretofore, by the use of cross metathesis catalysts results in the reaction of acyclic α-olefins with monocycloolefins, has produced a rather predictable mixture of symmetrical to unsymmetrical acyclic polyenes. Usually the ratio of symmetrical/unsymmetrical/symmetrical acyclic polyene mixture is in the range of 1/2/1. The present invention produces an unexpected mixture of symmetrical to unsymmetrical acyclic polyenes. Said unsymmetrical acyclic polyenes can be used in the preparation of EPDM polymers wherein an acyclic polyene is needed with a terminal double bond.

The reaction of 1-pentene with cyclopentene can form a mixture of cross metathesis products which are acyclic polyenes and can generally be described by the following series of formulas:

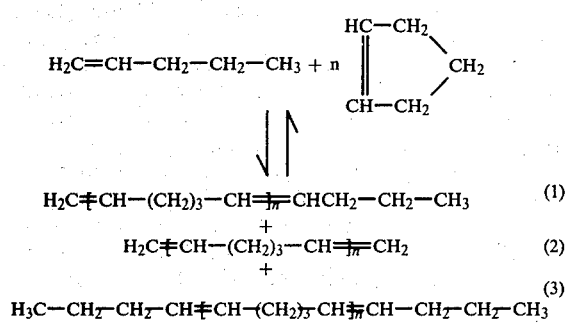

In the preparation of EPDM type polymers, however, it is highly desirable to have an acyclic polyene that has a single terminal double bond. In the present invention the predominant formation of unsymmetrical polyenes which correspond to the formula:

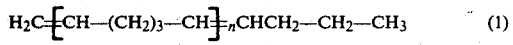

is the type of acyclic polyene that is desirable for this EPDM in use. By the term "predominant" is meant the unsymmetrical polyene with a single terminal double bond is produced at least as 75 percent of the cross metathesis polyenes.

Accordingly, the invention is directed to the cross metathesis reaction products acyclic polyene formed by bringing 1-pentene and cyclopentene into contact with a cross metathesis catalyst to form a predominance of acyclic polyenes responding to the formula:

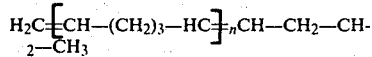

wherein n can be any positive integer.

Catalysts which are operable according to the present invention, i.e. for olefin cross metathesis, are those catalysts which will, when present in catalytic amounts, convert 2-pentene into a mixture of 2-butene and 3-hexene at ambient conditions.

One class of homogeneous catalyst systems employed in the practice of this invention is a system comprising (A) at least one organometallic compound wherein the metal is selected from the group consisting of Ia, IIa, IIb, IIIa and IVa of the Periodic Table of Elements, (B) at least one metal derivative wherein the metal is selected from the group consisting of molybdenum and tungsten and (C) at least one material selected from a group consisting of oxygen and compounds of the general formula R—Y—R', wherein Y is selected from the group of oxygen (O) and sulfur (S) and wherein R and R' are radicals selected from the group consisting of (1) hydrogen (H), (2) alkyl, (3) aryl, (4) arylalkyl, (5) alkaryl, (6) alkenyl, (7) halogenated alkyl, (8) halogenated aryl, (9) halogenated arylalkyl, (10) halogenated alkaryl, (11) halogenated alkenyl, (12) cyano alkyl, (13) cyano aryl, (14) cyano arylalkyl, (15) cyano alkaryl, (16) cyano alkenyl, (17) when Y is S and R' is H, then R can be thioalkyl, thioarylalkyl and thioalkaryl, (18) when Y is O and R' is H, then R can be alkoxy, arylalkoxy and alkaryloxy, and (19) radicals of (2) through (8) wherein at least one hydrogen is substituted by a group selected from hydroxyl (OH) and thiol (SH). The Periodic Table of Elements referred to may be found in the Handbook of Chemistry and Physics, 44th Edition, April 1962 reprint, published by the Chemical Rubber Publication Company, Cleveland, Ohio, U.S.A., p. 448.

Representative examples of metals from which the organometallic compound, the first or (A) component of the catalyst system of this invention, can be derived are lithium, sodium, potassium, rubidium, cesium, beryllium, magnesium, calcium, strontium, barium, zinc, cadmium, aluminum, gallium, indium, thallium and tin. The preferred organometallic compounds are compounds of lithium, sodium, magnesium, aluminum, zinc and tin, with aluminum and tin being most preferred.

Representative examples of organometallic compounds useful as the first or (A) catalyst component of this invention are aluminum compounds having at least one aluminum-to-carbon bond. Representative of such compounds are trialkylaluminums such as trimethylaluminum, triethylaluminum, tri-n-propylaluminum, tri-n-butylaluminum, triisopropylaluminum, triisobutylaluminum, trihexylaluminum, trioctylaluminum, and the like; triarylaluminums such as tritolylaluminum, tribenzylaluminum, triphenylaluminum, and the like; dialkylaluminum halides such as diethylaluminum chloride, di-n-propylaluminum chloride, diisobutylaluminum chloride, diethylaluminum bromide, diethylaluminum iodide and diethylaluminum fluoride and the like; mixtures of dialkylaluminum halides and alkylaluminum dihalides such as ethylaluminum sesquichloride and bromide may also be employed; alkylaluminum dihalides such as ethylaluminum dichloride, ethylaluminum dibromide, propylaluminum dichloride, isobutylaluminum dichloride, ethylaluminum diiodide and the like; dialkylaluminum hydrides such as diethylaluminum hydride, di-n-propylaluminum hydride, diisobutylaluminum hydride, and the like; arylaluminum hydrides and dihydrides such as diphenylaluminum hydride and phenylaluminum dihydride, the arylaluminum halides such as phenylaluminum dibromide, tolylaluminum dibromide, benzylaluminum dibromide, phenylaluminum diiodide, tolylaluminum diiodide, benzylaluminum diiodide, diphenylaluminum chloride, ditolylaluminum chloride, dibenzylaluminum bromide, and the like. Other organometallic compounds are also useful in the practice of this invention. Representative of such organometallic compounds are organoalkali metal compounds such as alkyllithium compounds as ethyllithium, n-butyllithium, t-butyllithium and the like; lithium aluminum tetraalkyls such as lithium aluminum tetrabutyl, lithium aluminumtetraethyl, and the like; alkali metal alkyls and aryls such as amylsodium, butylpotassium, phenylpotassium, phenylsodium, phenyllithium, butyllithium and the like; magnesium alkyls and aryls such as diphenylmagnesium, diethylmagnesium, ethylmagnesium chloride, phenylmagnesium chloride, butylmagnesium bromide, and the like; calcium, strontium and barium organo compounds such as barium alkyls and aryls of Groups IIb metals such as diethylzinc, diphenylzinc, ethylzinc chloride, diethylcadmium, dibutylcadmium, and the like. Grignard agents such as phenylmagnesium bromide may also be employed. Organotins, such as tetraalkyltin, tetraarylalkyltin, trialkyltin halides and triaryltin halides and triaryltin halides may also be employed as an organometallic compound. Representative of such organotin compounds are tetramethyltin, tetrabutyltin, tetrabenzyltin, triethyltin chloride, triphenyltin chloride and the like. Mixtures of these compounds may be employed as the first or (A) catalyst component in the catalyst of this invention. It is usually preferred to employ aluminum compounds such as trialkylaluminums, dialkylaluminum halides, alkylaluminum dihalides and alkylaluminum sesquihalides.

The metal derivatives employed in the catalyst of this invention as the second or (B) catalyst component are selected from the derivatives of molybdenum and tungsten. Representatives of such derivatives include halides such as chlorides, bromides, iodides and fluorides, which include compounds such as molybdenum pentachloride, tungsten hexachloride, molybdenum pentabromide, tungsten hexabromide, molybdenum pentaiodide, molybdenum pentafluoride, molybdenum hexafluoride and tungsten hexafluoride. Other representative salts are those of acetylacetonates, sulphates, phosphates, nitrates and the like which include compounds such as molybdenum phosphate, tungsten phosphate, molybdenum nitrate, tungsten nitrate, molybdenum acetylacetonate, tungsten acetylacetonate, molybdenum sulphate, and tungsten sulphate. Mixtures of these salts may also be employed. Of these, it is usually preferred to employ tungsten halides and molybdenum halides, representative of which are tungsten hexachloride and molybdenum pentachloride.

The third component or (C) component of the catalyst system of this invention is selected from the group consisting of oxygen and compounds which respond to the formula R—Y—R' wherein Y is selected from the group consisting of oxygen and sulfur and R and R' are radicals selected from the group consisting of (1) hydrogen, (2) alkyl, (3) aryl, (4) arylalkyl, (5) alkaryl, (6) alkenyl, (7) halogenated alkyl, (8) halogenated aryl, (9) halogenated arylalkyl, (10) halogenated alkaryl, (11) halogenated alkenyl, (12) cyano alkyl, (13) cyano aryl, (14) cyano arylalkyl, (15) cyano alkaryl, (16) cyano alkenyl, (17) when Y is S and R' is H, then R can be thioalkyl, thioarylalkyl and thioalkaryl, (18) when Y is O and R' is H, then R can be alkoxy, arylalkoxy and alkaryloxy, and (19) radicals of (2) through (8) wherein at least one hydrogen is substituted by a group selected from hydroxyl (OH) and thiol (SH).

Thus, the formula R—Y—R' above defines a number of types of compounds. It defines water (HOH), hydrogen sulfide (HSH), both saturated and unsaturated alcohols (ROH), mercaptans, (RSH), hydroperoxides (ROOH), hydrodisulfides (RSSH), polyalcohols (HOROH), polymercaptans (HSRSH), hydroxy mercaptans (HSROH) or thioalcohols (HORSH) and ethers and thioethers. Representative examples of the materials corresponding to the formula above are alcohols representative of which are methanol, ethanol, isopropanol, tertiarybutyl alcohol, amyl alcohol, benzyl alcohol, allyl alcohol, 1,1-dimethyl benzyl alcohol, phenol, tertiarybutyl catechol, alpha and beta naphthyl alcohol; mercaptans such as methyl, ethyl, propyl, isopropyl, butyl, amyl and similar mercaptans, allyl mercaptan, thiophenol, 4-methylthiophenol, 4-mercaptoxylene; the hydroperoxides such as cumyl hydroperoxide, tertiarybutyl hydroperoxide; the hydrodisulfides such as cumyl hydrodisulfide, s-butyl hydrodisulfide, the polyalcohols such as ethylene glycol, glycerol, and similar polyglycols; catechol, resorcinol, hydroquinone, pyrogallol; the polymercaptans such as 1,3-propane dithiol, 1,4-dimercaptobenzene, the hydroxymercaptans or thioalcohols such as 2-mercaptoethanol and p-mercaptophenol; ethers such as dimethylether, diethylether, dibutyl ether, and anisole.

Other materials which can function as the third component (C) are described in recent literature (Symposium on Polymerization and Related Reactions, Polymer Preprints, Vol. 13, No. 2, pp. 874–923 (1972), American Chemical Society Meeting, September 1972).

It has been found that good results are obtained in the practice of this invention when the molar relationship between the three catalyst components (A), (B) and (C) as previously defined, are within a molar ratio of (B)/(C) ranging from about 0.2/1 to at least about 20/1 and the molar ratio of (A)/(B) is within the range of about 0.5/1 to at least 15/1. More preferred ratios are (B)/(C) of 0.5/1 to 5/1 and (A)/(B) of 0.5/1 to 8/1. Still more preferred ratios are (B)/(C) of 1/1 to 2/1 and (A)/(B) of 0.75/1 to 5/1.

The ratio of the acyclic alphaolefin/monocycloolefin can range from about 0.5/1 to about 100/1. A more preferred ratio is from about 0.5/1 to about 20/1. The most preferred range of acrylic alphaolefin/monocycloolefin is from about 0.5/1 to about 3/1.

The amount of catalyst employed in the reactions of this invention may be varied over wide concentrations and has not been found to be critical. Of course, a catalytic amount of the catalyst must be employed. The optimum amount of catalyst depends upon a number of factors such as temperature, purity of reactants, reaction times desired, and the like. The processes of this invention can be conducted wherein the amount of catalyst employed is about 0.01 part by weight of component (B) per 100 parts by weight of unsaturated reactants employed, with components (A) and (C) adjusted to yield a desirable molar ratio of (A)/(B)/(C). Those skilled in the art will readily be able to determine the optimum catalytic ranges.

A second class of catalyst systems effective in the present invention consists of a two-component catalyst system. This catalyst system comprises (A) at least one organoaluminum halide selected from the group consisting of $RAlX_2$ and $R_2AlX$ wherein X is a halide such as chloride, bromide, iodide, and fluoride, and R is selected from the group of alkyl, aryl, arylalkyl and alkaryl, and (B) at least one tungsten derivative.

Thus, representative examples of the first or (A) catalyst component are aluminum compounds having at least one aluminum-to-carbon bond. Representative of such compounds are dialkylaluminum halides such as diethylaluminum chloride, di-n-propylaluminum chloride, diisobutylaluminum chloride, diethylaluminum bromide, diethylaluminum iodide and diethylaluminum fluoride, and the like; mixtures of dialkylaluminum halides and alkylaluminum dihalides such as ethylaluminum sesquichloride and bromides may also be employed; alkylaluminum dihalides such as ethylaluminum dichloride, ethylaluminum dibromide, propylaluminum dichloride, isobutylaluminum dichloride, ethylaluminum diiodide, and the like; the arylaluminum halides such as phenylaluminum dibromide, tolylaluminum dibromide, benzylaluminum dibromide, phenylaluminum diiodide, tolylaluminum diiodide, benzylaluminum diiodide, diphenylaluminum chloride, ditolylaluminum chloride, dibenzylaluminum bromide, and the like.

Representative of the tungsten salts employed as the second or (B) catalyst component include halides such as chlorides, bromides, iodides, and fluorides, which include compounds such as tungsten hexachloride, tungsten hexabromide, tungsten hexaiodide, and tungsten hexafluoride. Other representative salts are those of acetylacetonates, sulphates, phosphates, nitrates and the like which include compounds such as tungsten phosphate, tungsten nitrate, tungsten acetylacetonate and tungsten sulphate. Mixtures of these salts may also be employed. Of these, it is usually preferred to employ tungsten halides such as tungsten hexachloride.

The molar relationship between the two catalyst components (A) and (B) as previously defined in this catalyst system are within a molar ratio of (A)/(B) of about 0.5/1 to about 15/1 with a more preferred molar ratio of (A)/(B) of about 0.5/1 to about 8/1 and a still more preferred molar ratio of (A)/(B) of about 0.75/1 to about 5/1. These catalysts can be prepared by "in situ" or "preformed" techniques. No particular order of addition is required in preparing active catalysts from this species. These catalyst components may be reacted together as pure compounds or in solutions or suspensions in inert liquids. Representative of such liquids are saturated hydrocarbons such as benzene, toluene and the like.

The amount of catalyst employed in the reactions of the present invention, when this two-component catalyst system is employed, has not been found to be critical and may range over wide concentrations. Of course, a catalytic amount of the catalyst must be employed but the optimum amount depends upon a number of factors such as temperature employed, the particular reactants employed, the purity of the reactants, the reaction times desired, and the like.

A third class of catalyst systems effective in promoting the processes of the present invention consists of (A) an aluminum halide, $AlX_3$, and (B) a salt of the transition metal tungsten, whereby the tungsten is at any oxidation status within the IV to VI range.

Representative examples of component (A) are: aluminum chloride, aluminum bromide, aluminum iodide and aluminum fluoride. The preferred halides are the chloride and bromide of aluminum. Examples of component (B) are: tungsten tetra-, penta- and hexachlorides, tungsten tetra- and pentabromides, tungsten tetra- and pentaiodides, tungsten hexafluoride and the tungsten oxychlorides. This two component catalyst system is unique as it does not require the employment of any organometallic catalyst component. However, this system can be further modified by an organometallic reagent. (In certain reactions of unsaturated alicyclic compounds, advantages such as suppression of gel formation, and an increase in polymerization rates at lower catalyst levels can be achieved by the modification of the last two-component catalyst system by an optional third organometallic reagent). Examples of such optional organometallic reagents are organoalkali metal compounds such as alkyl- and aryllithium; alkyl- and arylsodium; organomagnesium compounds such as dialkyl- or diarylmagnesium, organomagnesium halides; organometallic derivatives of calcium, strontium and barium; alkyls and aryls of Groups IIb metals such as dialkyl- and diarylzinc and the like.

The polymerizations can be conducted in inert solvents such as benzene, toluene, hexane, cyclohexane and the like. By the term "inert solvent" is meant any solvent that does not adversely affect the mixture of polyenes formed by this invention.

The reaction temperatures are not particularly critical and may be conducted over a temperature range of from about $-10°$ C. to about $100°$ C. A more preferred temperature range is from about $-5°$ C. to about $40°$ C.

EXPERIMENTAL

Ethylaluminum dichloride (EADC) and diethyl chloride (DEAC) were diluted in benzene to form 0.2 molar (M) solutions.

Tungsten hexachloride ($WCl_6$) was used without prior purification along with the catalytic modifiers 2,2,2-trichloroethanol ($Cl_3CCH_2OH$) and 2-chloroethanol ($ClCH_2CH_2OH$).

Cyclopentene and 1-pentene were purified by distillation and treated by passing over activated silica gel prior to use.

Analysis was by gas liquid chromatography performed on an F&M 810 model gas Chromatograph.

Catalyst Preparation

An 0.05 M solution of $WCl_6$ in benzene was prepared by dissolving 1.0 grams $WCl_6$ and 50 mils of dried benzene. Appropriate amounts of the alcoholic modifier were added to the tungsten solution in order to have a $WCl_6$/alcoholic molar ratio of ½ and allowed to react at room temperature for a minimum period of 30 minutes prior to use.

Further practice of this invention is illustrated by reference to the following examples which are intended to be illustrative and in no way limiting the scope of this invention.

EXAMPLE I

Cyclopentene and 1-pentene monomer were purified by distillation and treated by passing over activated silica gel prior to use. The monomers were then syringed under a nitrogen atmosphere into 2-ounce polymerization bottles equipped with self-sealing gaskets and teflon liners. A known quality of n-nonane was added to each bottle to serve as an internal standard for analytical purposes and the mixture was sparged with nitrogen. This mixture was analyzed on a gas chromatograph for quantitative composition. Thus, to 3.8 g. (0.056 mole) cyclopentene and 9.5 g. (0.135 mole) 1- pentene, maintained at either 0° or 25° C. were added by hypodermic syringe 1.0 ml. of 0.05 molar tungsten hexachloride ($WCl_6$)-trichloroethanol ($Cl_3CCH_2OH$) solution, followed by 0.75 ml. of 0.2 molar ethyl aluminum dichloride ($C_2H_5AlCl_2$) solution. The reactions were shortstopped at the appropriate time by the addition of 0.1 ml. methanol and the product composition of the mixture was determined.

Column 1 is the Experiment number; column 2 is temperature in °C.; column 3 is the amount of unreacted cyclopentene after the metathesis reaction; column 4 is the amount of cyclopentene which was converted to unsymmetrical polyenes; column 5 is the amount of unsymmetrical polyene which was determined as a weight percent by the gas chromatograph of the product mixture up to 28 carbon atoms; column 6 is the amount of cyclopentene which was undetectable under the limitations of direct observation up to $C_{28}$, however, with the knowledge of the observed product distribution one can extrapolate to higher molecular weight members of the series which are beyond direct observation but should follow the same product distribution in order to account for the remaining cyclopentene; and column 7 is the total amount of selectivity based on the amounts of cyclopentene which was initially charged.

TABLE 1

| | | CONVERSION OF CYCLOPENTENE INTO POLYENES (%) | | | | |
|---|---|---|---|---|---|---|
| Exp. No. | Temp. °C. | Unreacted Cyclopentene | Cyclopentene in Unsymmetric Polyenes: $C_{10}, C_{15}, C_{20}, C_{25}$ | Unsymmetric Polyenes as Wt. % Product Mixture up to $C_{28}$ | Cyclopentene in Other Products | Total % Selectivity |
| 1$^{(a)}$ | (0°) | 67 | 26.6 | 93 | 6.4 | 80.6 |
| 1$^{(b)}$ | (25°) | 72 | 21.2 | 91 | 6.8 | 75.7 |
| 2$^{(a)}$ | (0°) | 21 | 67.5 | 75 | 11.5 | 85.4 |
| 2$^{(b)}$ | (25°) | 67 | 18.0 | 77 | 15.0 | 54.5 |
| 3$^{(a)}$ | (0°) | 70 | 11.1 | 85 | 18.9 | 36.6 |
| 3$^{(b)}$ | (25°) | 58 | 19.1 | 93 | 22.9 | 45.3 |
| 4$^{(a)}$ | (0°) | 64 | 12.3 | 93 | 23.7 | 34.1 |
| 4$^{(b)}$ | (25°) | 54 | 27.7 | 90 | 18.3 | 60.5 |

Exp. 1$^{(a)}$ & $^{(b)}$ - neat; 1-pentene/cyclopentene = 2.4/1; EADC/$WCl_6$/$CCl_3CH_2OH$: reaction 30 min.
Exp. 2$^{(a)}$ & $^{(b)}$ - 50% benzene; 1-pentene/cyclopentene = 0.77/1; EADC/$WCl_6$/$CCl_3CH_2OH$: reaction 30 min.
Exp. 3$^{(a)}$ & $^{(b)}$ - 50% benzene; 1-pentene/cyclopentene = 4.7/1; EADC/$WCl_6$/$ClCH_2CH_2OH$: reaction 60 min.
Exp. 4$^{(a)}$ & $^{(b)}$ - 50% benzene; 1-pentene/cyclopentene = 4.7/1; DEAC/$WCl_6$/$ClCH_2CH_2CH$: reaction 60 min.

The total distribution of symmetrical/unsymmetrical/symmetrical polyenes could not be measured to the complete accuracy because the symmetrical polyenes were present in their trace amounts. However, it is suggested that the distribution of symmetrical/unsymmetrical polyenes in the trace amounts is approximately the same as that which appears in the majority of the observed product mixture which is given in the above Table 1. It is shown in Table 1 that the majority of the polyenes are unsymmetrical as an illustration of the present invention. There is no reason to believe that the unresolvable amounts of product mixture would be any different than that which is shown by the above data.

It can be seen that although all of the cyclopentene may not have been reacted, that which was reacted to a product mixture of polyenes went to predominately unsymmetrical polyenes, as illustrated in column 5.

While certain representative embodiments and details have been shown for the purpose of illustrating the invention, it will be apparent to those skilled in this art that various changes and modifications may be made therein without departing from the spirit or scope of the invention.

What is claimed is:

1. A method of preparing a polyene product comprised of a symmetrical/unsymmetrical/symmetrical polyene mixture and containing at least 75 weight percent unsymmetrical polyene with a single terminal double bond through a cross-metathesis reaction which comprises contacting a mixture of 1-pentene and cyclopentene, at a temperature in the range of about −5° C. to about 40° C. with a cross-metathesis catalyst which comprises (A) at least one compound selected from diethylaluminum chloride, dipropyl aluminum chloride, ethylaluminum dichloride, propylene aluminum dichloride and tetrabutyltin; (B) at least one metal derivative selected from tungsten hexachloride and tungsten hexafluoride and (C) at least one alcohol selected from 2-chloroethanol and 2,2,2,-trichloroethanol; where the molar ratio of A/B catalyst components is in the range of about 0.5/1 to about 8/1 and the molar ratio of B/C catalyst components is in the range of about 0.5/1 to about 5/1 and where the molar ratio of the monomers 1-pentene/cyclopentene is in the range of about 0.5/1 to about 20/1.

2. The method of claim 1 where catalyst compound (A) is selected from at least one of ethylaluminum dichloride and diethylaluminum chloride and catalyst compound (B) is tungsten hexafluoride.

* * * * *